United States Patent [19]
Akhavan-Tafti

[11] Patent Number: 5,431,845
[45] Date of Patent: Jul. 11, 1995

[54] POLYMERIC PHOSPHONIUM SALTS PROVIDING ENHANCED CHEMILUMINESCENCE FROM 1,2-DIOXETANES

[75] Inventor: Hashem Akhavan-Tafti, Sterling Heights, Mich.

[73] Assignee: Lumigen, Inc., Southfield, Mich.

[21] Appl. No.: 194,517

[22] Filed: Feb. 10, 1994

Related U.S. Application Data

[62] Division of Ser. No. 855,537, Mar. 20, 1992, Pat. No. 5,393,469.

[51] Int. Cl.$^6$ .................. C09K 3/00; C09K 11/06; C08C 19/24
[52] U.S. Cl. .................. 252/700; 252/301.16; 252/301.35; 525/340
[58] Field of Search .................. 252/301.35, 301.16, 252/700; 525/340

[56] References Cited

U.S. PATENT DOCUMENTS

| | | | |
|---|---|---|---|
| 4,069,017 | 1/1978 | Wu | 23/230 B |
| 4,204,839 | 5/1980 | Wu | 23/230 B |
| 4,338,095 | 7/1982 | Wu | 252/700 |
| 4,446,284 | 5/1984 | Parker | 525/340 |
| 4,842,977 | 7/1989 | Kakimi | 430/138 |
| 4,857,652 | 8/1989 | Schaap | 252/700 |
| 4,927,769 | 5/1990 | Chang | 252/700 |
| 4,931,223 | 6/1990 | Bronstein | 252/700 |
| 4,952,707 | 8/1990 | Bronstein | 252/700 |
| 4,959,182 | 9/1990 | Schaap | 252/700 |
| 4,978,614 | 12/1990 | Bronstein | 252/700 |
| 5,004,565 | 4/1991 | Schaap | 252/700 |
| 5,013,827 | 5/1991 | Schaap | 252/700 |
| 5,032,381 | 7/1991 | Bronstein | 252/700 |

FOREIGN PATENT DOCUMENTS

| | | |
|---|---|---|
| 8233 | 2/1980 | European Pat. Off. . |
| 63-243964 | 11/1988 | Japan . |
| 2162946 | 7/1988 | United Kingdom . |
| 8914749 | 1/1991 | United Kingdom . |
| 8800695 | 1/1988 | WIPO . |
| 8906380 | 7/1989 | WIPO . |

OTHER PUBLICATIONS

T. P. Whitehead et al., Nature 158 (1983).
L. J. Kricka et al., Pure and Appl. Chem., 59(5) 651 (1987).
Thorpe, H. G., et al., Biolumin.&Chemilumin New Perspectives, John Wiley & Sons, Chichester, p. 199 (1987).
Gundermann, K. D., Biolumin. & Chemilumin., Academic Press, New York, p. 17 (1981).
Metelitza, D. I., et al., J. Biolumin. & Chemilumin. 7,21 (1992).
T. Goto et al., Tetrahedron Lett., 4299 (1969).
Kricka, L. J. et al., Arch. Biochem. Biophys. 217, 674 (1982).
McCapra, F., Acc. Chem. Res. 9, 201 (1976).
Schaap, A. P. et al., Amer. Chem. Soc. 104, 3504 (1982).
Schaap, A. P., et al., Tetrahedron Lett., 1155 (1987).
Schaap, A. P., et al., Tetrahedron Lett., 935 (1987).
Schaap, A. P., et al., Tetrahedron Lett, 1159 (1987).
Wilson, T., Int. Rev. Sci.:Chem., Ser. Two 9, 265 (1976).
Wilson, T., et al., J. Amer. Chem. Soc., 95, 4765 (1973).
Barlett, P. D., et al., Amer. Chem., Soc., 96, 5557 (1974).
Schaap, A. P., Photochem. Photobiol., 47S, 50S (1988).
Shinkai, S., et al., Chem. Lett., 1523 (1981).
Schaap, A. P., et al., Clin. Chem., 35(9), 1863 (1989).
Pollard-Knight, D., et al., Anal. Biochem., 185, 353 (1990).
Clyne, J. M., et al., J. Biolumin. Chemilumin. 2, 193 (1988).
Oberfelder, R., Focus, 13, 50 (1991).
Sandhu, G. S., et al., BioTechniques 11, 14 (1991).
Laemmli, U. K., Nature (London), 227, 680 (1970).

*Primary Examiner*—Philip Tucker
*Attorney, Agent, or Firm*—Ian C. McLeod

[57] ABSTRACT

Polymeric phosphonium salts useful for enhancing the chemiluminescence produced by 1,2-dioxetanes are described. The polymers are preferably water soluble and used in immunoassays and nucleic acid assays with enzyme triggerable 1,2-dioxetanes.

6 Claims, 8 Drawing Sheets

POLYMERIC PHOSPHONIUM SALTS PROVIDING ENHANCED CHEMILUMINESCENCE FROM 1,2-DIOXETANES

This is a divisional of application Ser. No. 07/855,537 filed on Mar. 20, 1992, now U.S. Pat. No. 5,393,469.

BACKGROUND OF THE INVENTION

1. State of the Invention

The present invention describes a class of enhancer polymers used with light producing 1,2-dioxetanes to produce enhanced chemiluminescence. Enhancers are substances which increase the amount of chemiluminescence emitted by the 1,2-dioxetane. The enhancer polymer can act to increase the fluorescence quantum yield of the 1,2-dioxetane and can include a fluorescent energy acceptor compound which is excited by an excited species produced in the decomposition of the 1,2-dioxetane and then emits light. The enhancer can act to increase the percentage of 1,2-dioxetane molecules which produce an electronically excited state product and thus more light. For the purposes of this invention, enhanced chemiluminescence means that the total light emitted, the maximum light intensity and/or the ratio of light intensity of the reaction compared to the background is greater than that observed in the absence of the enhancer. A preferred 1,2-dioxetane reaction is as follows:

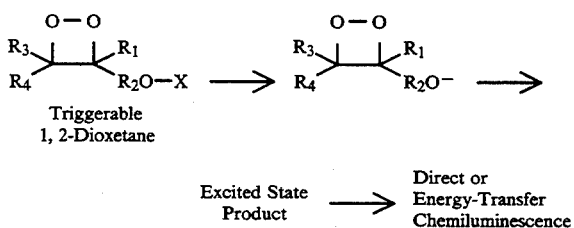

wherein $R_1$, $R_3$ and $R_4$ are various organic groups and $R_2$ is an aryl group substituted with OX(X-oxy) group.

2. Prior Art

1. Enhancers of Chemiluminescent Reactions not Involving Dioxetanes

Various substances are known including 4-substituted phenols, 6-hydroxybenzothiazole and its derivatives and several aromatic amines which enhance the chemiluminescent output from the oxidation of luminol by a peroxide in the presence of a peroxidase enzyme (European Patent No. 0087959; U.K. Patent Application GB 2162946A: T. P. Whitehead et al, Nature 158 (1983)). The nature of the enhancement is not well understood but is thought to be due to the enhancer substance acting as a redox mediator in the enzymatic reaction (L. J. Kricka, G. H. G. Thorpe and R. A. W. Stott, Pure and Appl. Chem., 59(6), p. 651 (1987); G. H. G. Thorpe and L. J. Kricka, Bioluminescence and Chemiluminescence New Perspectives, John Wiley & Sons, Chichester, p. 199 (1987)). Enhancement is in any case, not thought to be due to an increase in the fluorescence quantum yield of the excited aminophthalate product nor due to energy transfer to a fluorescer nor to an increase in the yield of chemically produced excited states.

2. Enhancement by Surfactants of Chemiluminescence not involving Dioxetanes

Enhancement by surfactants of the chemiluminescent oxidation of luminol (K. D. Gundermann, Biolumines- cence and Chemiluminescence, Academic Press, New York, p. 17 (1981); D. I. Metelitza, A. N. Eryomin and V. A. Shibaev, J. Biolumin. and Chemilumin., 7, 21 (1982)) has been reported. Chemiluminescence from the chemical oxidation of luciferin was found to increase in the presence of various surfactants due to an increase in the fluorescence quantum yield of the excited state product (T. Goto and H. Fukatsu, Tetrahedron Lett., 4299 (1969)). On the other hand, enzymatic oxidation of luciferin was found to increase in the presence of non-ionic surfactants due to an increase in the turnover rate of the enzyme (L. J. Kricka and M. DeLuca, Arch. Biochem. Biophys., 217, 674 (1983)). Enhancement of the chemiluminescent oxidation of acridinium esters by a cationic surfactant was reported to be due to suppression of a competing non-chemiluminescent side reaction (F. McCapra, Acc. Chem. Res., 9, 201 (1976)). U.S. Pat. No. 4,927,769 to Chang discloses various enhancers.

3. Chemical Triggering of Dioxetanes

The first example in the literature is described in relation to the hydroxy-substituted dioxetane derived from the 2,3-diaryl-1,4-dioxene (A. P. Schaap and S. Gagnon, J. Amer. Chem. Soc., 104, 3504 (1982)). However, the hydroxy-substituted dioxetane and any other examples of the dioxetanes derived from the diaryl-1,4-dioxenes are relatively unstable having half-lives at 25° C. of only a few hours. Further, these non-stabilized dioxetanes are destroyed by small quantities of amines (T. Wilson, Int. Rev. Sci.: Chem., Ser. Two, 9, 265 (1976)) and metal ions (T. Wilson, M. E. Landis, A. L. Baumstark, and P. D. Bartlett, J. Amer. Chem. Soc., 95, 4765 (1973); P. D. Barlett, A. L. Baumstark, and M. E. Landis, J. Amer. Chem. Soc., 96, 5557 (1974)), both components used in the aqueous buffers for biological assays.

Examples of the chemical triggering of stabilized dioxetanes were first reported in U.S. Pat. No. 4,857,652 to Schaap and a paper (A. P. Schaap, T. S. Chen, R. S. Handley, R. DeSilva, and B. P. Giri, Tetrahedron Lett., 1155 (1987)). These dioxetanes exhibit thermal half-lives of years but can be triggered to produce efficient chemiluminescence on demand.

4. Enzymatic Triggering of Dioxetanes

The first examples of enzymatic triggering of dioxetanes are described in U.S. Pat. No. 4,857,652 to Schaap and a series of papers (A. P. Schaap, R. S. Handley, and B. P. Giri, Tetrahedron Lett., 935 (1987); A. P. Schaap, M. D. Sandison, and R. S. Handley, Tetrahedron Lett., 1159 (1987) and A. P. Schaap, Photochem. Photobiol., 47S, 50S (1988)). The highly stable adamantyl-substituted dioxetanes bearing a protected hydroxyaryl substituent are triggered to decompose with emission of light by the action of an enzyme which removes the protecting group. The hydroxyaryl group is subsequently converted at pH>9 to a strongly electron-donating aryloxide anion which dramatically increases the rate of decomposition. As a result, chemiluminescence is emitted at intensities several orders of magnitude above that resulting from slow thermal decomposition. Bronstein PCT 88 00695 also describes enzyme triggerable dioxetanes as does Bronstein U.S. Pat. Nos. 4,948,614, 4,952,707, 5,032,381 and 4,931,223. It is anticipated that chemiluminescence from the triggerable dioxetanes described in these references can also be enhanced by the polymers of the present invention.

5. Fluorescent Enhancers Covalently Attached to Dioxetanes

Stable, triggerable dioxetanes with appended fluorescent groups are reported in U.S. Pat. No. 5,013,827 to Schaap. These compounds differ from the present invention in that enhancement of chemiluminescence occurs through a radiationless intramolecular energy transfer from the initially excited meta-oxybenzoate chromophore to a more highly fluorescent fluorophore.

6. Enhanced Chemiluminescence From Dioxetanes in the Presence of Surfactants

A chemiluminescent reaction believed to involve a non-isolable dioxetane was enhanced in micellar solution (S. Shinkai, Y. Ishikawa, O. Manabe and T. Kunitake, Chem. Lett., 1523 (1981)). The mechanism of enhancement remains unproven but the authors suggested that the yield of excited state products may be increased in the hydrophobic micellar environment as compared to water.

Schaap et al first reported the enhancement of chemiluminescence from the enzyme-triggered decomposition of a stable 1,2-dioxetane in the presence of water-soluble substances including an ammonium surfactant and a fluorescer. Fluorescent micelles consisting of cetyltrimethylammonium bromide (CTAB) and 5-(N-tetradecanoyl)aminofluorescein capture the intermediate hydroxy-substituted dioxetane and lead to a 400-fold increase in the chemiluminescence quantum yield. Enhancement occurs by virtue of an efficient intermolecular energy transfer process from the anionic form of the excited state ester to the fluorescein compound which is held in close proximity and the hydrophobic environment of the surfactant (A. P. Schaap, H. Akhavan and L. J. Romano, Clin. Chem., 35(9), 1863 (1989)).

also reported that CTAB itself can enhance the chemiluminescence of dioxetane 1 (U.S. Pat. Nos. 4,959,182 and 5,004,565 to Schaap). The phosphate-protected dioxetane 1 (Lumigen® PPD) has proven commercially useful for the sensitive detection of alkaline phosphatase. Chemiluminescent detection using Lumi-Phos ® 530, a ready-to-use liquid formulation containing, has been employed in Southern blotting (D. Pollard-Knight, A. C. Simmonds, A. P. Schaap, H. Akhavan, and M. A. W. Brady, Anal. Biochem., 185, 353 (1990)), a microtiter plate based DNA probe sandwich assay (J. M. Clyne, J. A. Running, R. Sanchez-Pescador, D. Besemer, M. Stempien, A. P. Schaap, R. S. Stephens, and M. S. Urdea, J. Biolumin. Chemilumin. 2, 193 (1988)) and Western blotting (R. Oberfelder, Focus, 13, 50 (1991); G. S. Sandhu, B. W. Eckloff, B. C. Kline, BioTechnques 11, 14 (1991)).

U.S. Pat. No. 4,978,614 to Bronstein and U.K. Patent Application No. 89/14749.0 (GB 2,233,451A) disclose enhancement of dioxetane chemiluminescence by polymeric quaternary ammonium compounds alone or admixed with fluorescein. Other substances reported to enhance chemiluminescence include globular proteins such as bovine albumin, quaternary ammonium surfactants, nitrogen-containing polymers and polyethers. No phosphonium polymers are disclosed.

7. Polymeric Phosphonium Salts

Polyvinylbenzyltrimethylphosphonium salts, polyvinylbenzyltriethylphosphonium salts and polyvinylbenzyltributylphosphonium salts have not been reported. Polyvinylbenzyltrihexylphosphonium salts are disclosed in a patent prepared as a copolymer with divinyl-

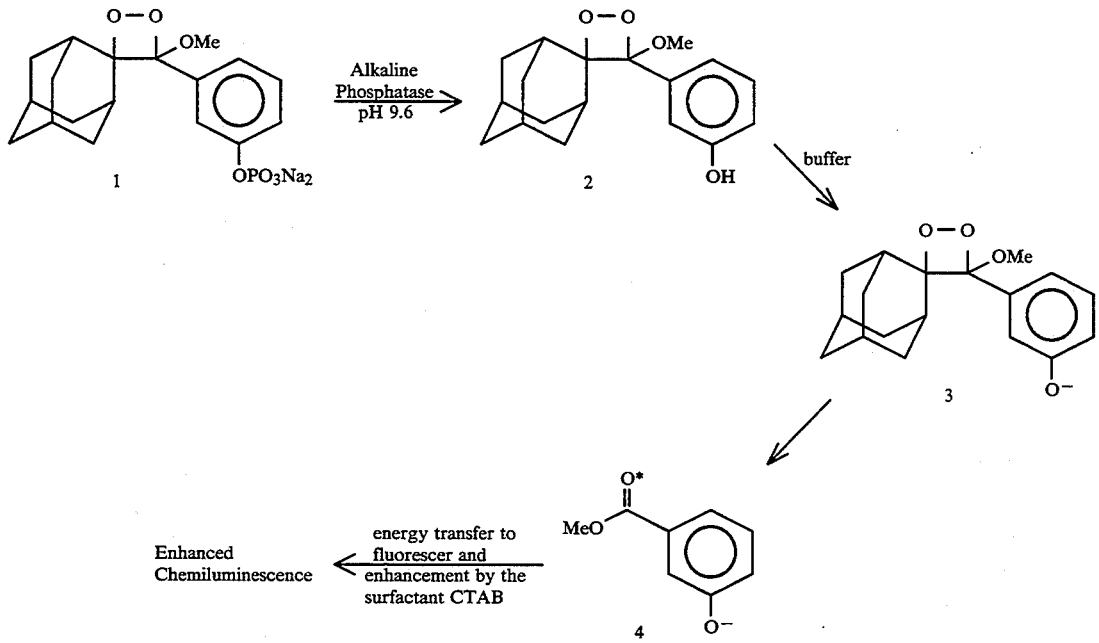

U.S. Pat. Nos. 4,959,182 and 5,004,565 to Schaap describe additional examples of enhancement of chemiluminescence from chemical and enzymatic triggering of stable dioxetanes in the presence of the ammonium surfactant and fluorescers.

Fluorescent micelles formed from CTAB and either the fluorescein surfactant described above or 1-hexadecyl-6-hydroxybenzothiaxamide enhance the chemiluminescence from the base-triggered decomposition of hydroxy- and acetoxy-substituted dioxetanes. It was benzene (PCT Int. Appl. WO 8906380 A1 13 Jul. 1989). Polyvinylbenzyldiethylphenylphosphonium salts are disclosed in a patent prepared as a copolymer with styrene (Jpn. Kokai Tokkyo Koho, JP 63243964 A2 11 Oct. 1988). Polyvinylbenzyltrioctylphosphonium salts are disclosed in a series of patents (U.S. Pat. No. 4,338,095 A 6 Jul. 1982 and EPA 28, 123 Eur. Pat. Appl. EP 8233 20 Feb. 1980, Eur. Pat. Appl. EP 28123 6 May 1981) as being useful for the fluorescent detection of bilirubin. Polyvinylbenzyltriphenylphosphonium salts are well known in the literature, being used as surfactants, phasetransfer catalysts and reagents in organic synthesis. Copolymers of polyvinylbenzyltriphenylphosphonium salts with acrylic acid, butadiene and divinylbenzene are known. None of the foregoing polymers or copolymers have been used as enhancers of chemiluminescence of 1,2-dioxetanes. No reports of covalently linked fluorescers to these polymeric phosphonium salts have been made. No polyvinylbenzyltrialkylphosphonium salts with mixed pendant groups have been reported.

OBJECTS

It is an object of the present invention to provide polymeric phosphonium salts, particularly watersoluble polyvinyl phosphonium salt polymers. It is also an object of the present invention to provide polymeric phosphonium salts to which fluorescent groups are attached through chemical bonds or associated by ionic or hydrophobic interactions. It is an object of the present invention to provide a method and compositions containing a stable 1,2-dioxetane which can be triggered by chemical reagents, including enzymes, in the presence of a polymeric phosphonium salt to generate enhanced chemiluminescence. Further, it is an object of the present invention to provide a method and compositions for additionally enhancing the chemiluminescence through energy transfer to a fluorescent compound or group which may be chemically bound to the polymer or associated with the polymer through ionic or hydrophobic interactions. Further the present invention relates to a method and compositions for the detection of enzymes, and for use in immunoassays and the detection of enzymelinked nucleic acids, antibodies and antigens such as are generally known in the art. These and other objects will become increasingly apparent by reference to the following description and the drawings.

GENERAL DESCRIPTION

Figure 1:
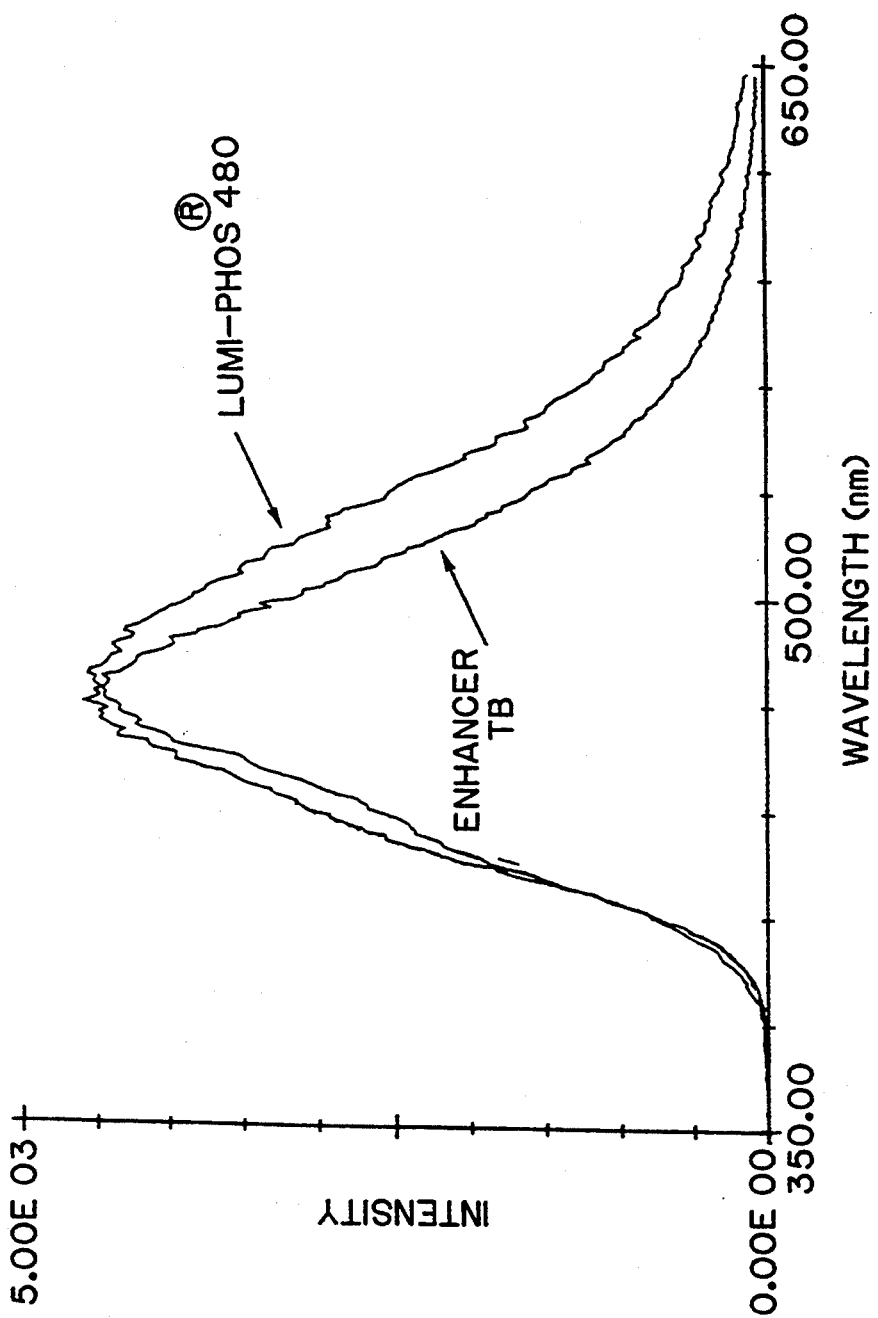
FIG. 1 is a graph showing a comparison of chemiluminescence spectra for an enzyme triggered 1,2-dioxetane with an enhancer of the present invention and in the commercial reagent LUMI-PHOS® 480. The graph shows alkaline phosphatase-triggered decomposition of dioxetane 1 (0.33 mM) in (a) Lumi-Phos® 480 and (b) 0.2 M 2-methyl-2-amino-1-propanol buffer, pH 9.6 containing 0.5 mg/mL TB. The wavelength of maximum emission of spectrum b is 470 nm. Lumi-Phos® 480 contains 0.75 M 2-methyl-2-amino-1-propanol buffer at pH 9.6 and 1.1 mM CTAB.

The present invention relates to a method for providing enhanced chemiluminescence from a stable 1,2-dioxetane in the presence of a polymeric phosphonium salt which comprises: providing in a solution or on a surface where the light is to be produced a stable 1,2-dioxetane and a polymeric phosphonium salt; and triggering the 1,2-dioxetane with an activating agent to provide the enhanced chemiluminescence. The method particularly relates to a probe or enzyme linked assay.

Further, the present invention relates to a composition which comprises: a stable 1,2-dioxetane; and a polymeric phosphonium salt wherein enhanced chemiluminescence is produced in a solution or on a surface in the presence of a sufficient quantity of the polymeric phosphonium salt compared to the chemiluminescence obtained in the absence of the polymeric phosphonium salt.

The present invention relates to a polyvinylLink-triAylphosphonium group containing polymer prepared by reacting triAyl phosphine with a polyvinyl polymer wherein Link is a linking group between the polymer and the phosphonium cation containing 1 to 20 carbon atoms and A is selected from the group consisting of alkyl containing 1 to 20 carbon atoms or alkyl and aralkyl groups each containing 1 to 20 carbon atoms.

The present invention relates to a polyvinylLink-triAylphosphonium and fluorescent group containing polymer wherein Link is a linking group between the polymer and the phosphonium cation containing 1 to 20 carbon atoms and A is selected from the group consisting of alkyl containing 1 to 20 carbon atoms or alkyl and aralkyl groups each containing 1 to 20 carbon atoms and wherein the fluorescent group is attached to the polymer.

The present invention further relates to a process for producing a polyvinyl phosphonium salt substituted polymer which comprises: reacting in a reaction mixture a polyvinylLink halide polymer with an triAyl phosphine in an organic solvent for the polyvinyl halide wherein A is selected from the group consisting of alkyl containing 1 to 20 carbon atoms or alkyl and aralkyl groups containing 1 to 20 carbon atoms; and separating the polymer from the reaction mixture. The reaction temperature is between about 0° and 100° C.

The present invention particularly relates to compositions containing a polymeric phosphonium salt and a stable 1,2-dioxetane which can be triggered by chemical reagents, including enzymes, to generate chemiluminescence. Stable dioxetanes useful in practicing the present invention may be of the formula:

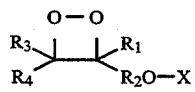

wherein $R_3$ and $R_4$ are organic groups which may be combined together and wherein $R_1$ is an organic group which may be combined with $R_2$, and wherein $R_2$ represents an aryl group substituted with an X-oxy group which forms an unstable oxide intermediate dioxetane compound when triggered to remove a chemically labile group X by an activating agent selected from acids, bases, salts, enzymes, inorganic and organic catalysts and electron donors. The OX group may be selected from hydroxyl, trialkyl or aryl silyloxy, inorganic oxyacid salt, phosphate salt, sulfate salt, oxygen pyranoside, aryl and alkyl carboxyl ester. The unstable oxide intermediate dioxetane decomposes and releases electronic energy to form light and two carbonyl containing compounds of the formula

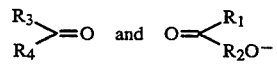

A preferred method of practicing the present invention uses a stable dioxetane of the formula:

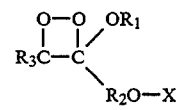

wherein $R_1$ is selected from lower alkyl or alkaryl containing 1 to 20 carbon atoms and may additionally contain heteroatoms, $R_3C$ is selected from spirofused cyclic and polycyclic organic groups containing 6 to 30 carbon atoms and may additionally contain heteroatoms and wherein $R_2$ is selected from aryl, biaryl, heteroaryl, fused ring polycyclic aryl or heteroaryl groups which can be substituted or unsubstituted and wherein OX is an X-oxy group which forms an unstable oxide intermediate dioxetane compound when triggered to remove a chemically labile group X by an activating agent selected from acids, bases, salts, enzymes, inorganic and organic catalysts and electron donors.

The present invention relates to compositions containing a stable 1,2-dioxetane which can be triggered by an activating agent to generate chemiluminescence in the presence of a polyvinyl phosphonium salt enhancer. Enhancers particularly useful in practicing the present invention are of the formula:

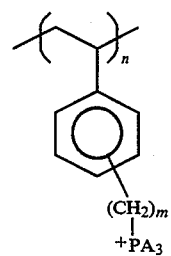

wherein A is selected from lower alkyl containing 1 to 20 carbon atoms, aryl or aralkyl groups, wherein m is an integer between 1 and 14, and wherein n and p are integers between about 10 and 1000. The A groups on a specific phosphorus atom may all be the same group or may be two different groups or all three may be different. The set of A groups on adjacent phosphorus atoms may be the same set or may be different sets wherein the sets are subject to the description above. The relative position of substituents on the aromatic ring may be ortho, meta, para or mixtures of the three types in any proportion.

The present invention particularly relates to compositions containing a stable 1,2-dioxetane which can be triggered by an activating agent to generate chemiluminescence in the presence of a polyvinyl phosphonium salts with fluorescent groups attached according to the formula:

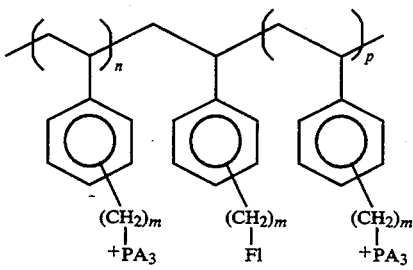

wherein A is selected from lower alkyl containing 1 to 20 carbon atoms, aryl or aralkyl groups, wherein m is an integer between 1 and 14, and wherein n and p are integers between about 10 and 1000. The A groups on a specific phosphorus atom may all be the same group or may be two different groups or all three may be different. The set of R groups on adjacent phosphorus atoms may be the same set or may be different sets wherein the sets are subject to the description above. The relative position of substituents on the aromatic ring may be ortho, meta, para or mixtures of the three types in any proportion. The attached fluorescent group may be any fluorescer which can be chemically linked to a polymer and which has a lower energy for its singlet electronic excited state compared to the excited state of the dioxetane product. The fluorescent group enhances the chemiluminescence efficiency of the dioxetane by acting as an energy acceptor which becomes excited and releases the excitation energy in the form of light. Examples of fluorescers useful in practicing the present invention include but is not limited to any fluorescent dye; aromatic compounds including polycyclic aromatic compounds, biphenyls, terphenyls, stilbenes, heteroaromatic and polycyclic heteroaromatic compounds such as acridines, coumarins, phthalocyanines, furans, oxazoles, oxadiazoles, benzothiazoles, quinolines, xanthenes, fluorescein and fluorescein derivatives, e.g. amidofluorescein, eosin and eosin derivatives, rhodamines and resorufins.

The present invention relates to polyvinyl phosphonium salts of the formula:

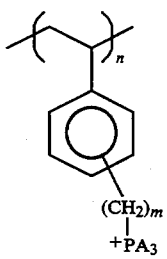

wherein A is selected from the lower alkyl containing 1 to 20 carbon atoms, aryl or aralkyl groups, wherein m is an integer between 1 and 14, and wherein n and p are integers between about 10 and 1000. The A groups on a specific phosphorus atom may all be the same group or may be two different groups or all three may be different. The set of A groups on adjacent phosphorus atoms may be the same set or may be different sets wherein the sets are subject to the description above. The relative position of substituents on the aromatic ring may be ortho, meta, para or mixtures of the three types in any proportion.

The present invention also relates to polyvinyl phosphonium salt polymers with fluorescent groups attached according to the formula:

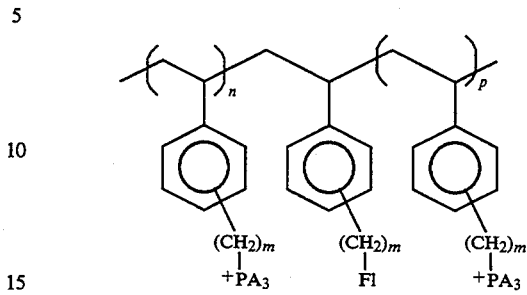

wherein A is selected from lower alkyl containing 1 to 20 carbon atoms, aryl, aralkyl or alkyaryl groups, wherein m is an integer between 1 and 14, and wherein n and p are integers between about 10 and 1000. The A groups on a specific phosphorus atom may all be the same group or may be two different groups or all three may be different. The set of A groups on adjacent phosphorus atoms may be the same set or may be different sets wherein the sets are subject to the description above. The relative position of substituents on the aromatic ring may be ortho, meta, para or mixtures of the three types in any proportion. The attached fluorescent group may be any fluorescer which can be chemically linked to a polymer and which has a lower energy for its singlet electronic excited state compared to the excited state of the dioxetane product. The fluorescent group enhances the chemiluminescence efficiency of the dioxetane by acting as an energy acceptor which becomes excited and releases the excitation energy in the form of light. Examples of fluorescers useful in practicing the present invention include but is not limited to any fluorescent dye; aromatic compounds including polycyclic aromatic-compounds, biphenyls, terphenyls, stilbenes, heteroaromatic and polycyclic heteroaromatic compounds such as acridines, coumarins, phthalocyanines, furans, oxazoles, oxadiazoles, benzothiazoles, quinolines, xanthenes, fluorescein and fluorescein derivatives, e.g. amidofluorescein, eosin and eosin derivatives, rhodamines and resorufins. An especially useful enhancer utilizes fluorescein as the covalently attached fluorescer. The amount of fluorescer groups attached to the polymer may range from about 0.001% to about 10% (W/W) and preferably from about 0.01% to about 1%.

The present invention also relates to compositions in which the amount of chemiluminescence emitted by the dioxetane in the presence of the polymeric phosphonium salt enhancer is greater than the amount of light emitted in the absence of the enhancer substance. The degree of enhancement is dependent upon the nature of the A groups substituting the phosphorus atoms. The degree of enhancement is also dependent on the concentration of enhancer used. Amplification of the chemiluminescence intensity occurs with enhancer concentrations ranging between about 0.001% and about 10%. Enhancers are preferably used at concentrations between about 0.01% and about 0.1% by weight.

The present invention relates to an improved method for generating light which comprises providing a polyvinyl phosphonium salt enhancer in the presence of a stable 1,2-dioxetane of the formula:

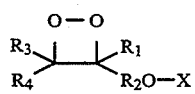

wherein $R_3$ and $R_4$ are organic groups which may be combined together, wherein $R_1$ is an organic group which may be combined with $R_2$ and wherein $R_2$ represents an aryl group substituted with an X-oxy group which forms an unstable oxide intermediate dioxetane compound when triggered to remove a chemically labile group X by an activating agent selected from acids, bases, salts, enzymes, inorganic and organic catalysts and electron donors. The OX group may be selected from hydroxyl, trialkyl or aryl silyloxy, inorganic oxyacid salt, phosphate salt, sulfate salt, oxygen pyranoside, aryl and alkyl carboxyl ester. The unstable oxide intermediate dioxetane decomposes and releases electronic energy to form light and two carbonyl containing compounds of the formula:

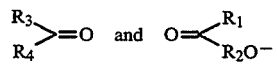

which can be triggered by an activating agent to generate chemiluminescence in the presence of a polymeric phosphonium salt.

The present invention relates to an improved method for generating light which comprises providing a stable 1,2-dioxetane which can be triggered by an activating agent to generate chemiluminescence in the presence of a polyvinyl phosphonium salt enhancer. Enhancers useful in practicing the present invention may be of the formula:

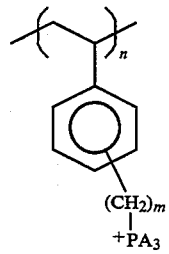

wherein A is selected from lower alkyl containing 1 to 20 carbon atoms, aryl or aralkyl groups, wherein m is an integer between 1 and 14, and wherein n and p are integers between about 10 and 1000. The A groups on a specific phosphorus atom may all be the same group or may be two different groups or all three may be different. The set of A groups on adjacent phosphorus atoms may be the same set or may be different sets wherein the sets are subject to the description above.

The present invention relates to an improved method for generating light which comprises providing a stable 1,2-dioxetane which can be triggered by an activating agent to generate chemiluminescence in the presence of a polyvinyl. phosphonium salt with fluorescent groups (Fl) attached according to the formula:

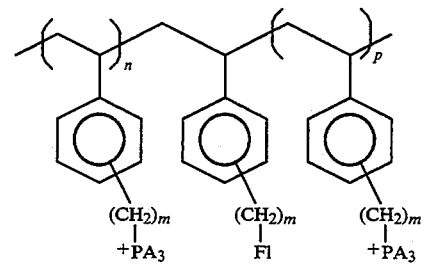

wherein A is selected from lower alkyl containing 1 to 20 carbon atoms, aryl or aralkyl groups, wherein m is an integer between 1 and 14, and wherein n and p are integers between about 10 and 1000. The A groups on a specific phosphorus atom may all be the same group or may be two different groups or all three may be different. The set of A groups on adjacent phosphorus atoms may be the same set or may be different sets wherein the sets are subject to the description above. The relative position of substituents on the aromatic ring may be ortho, meta, para or mixtures of the three types in any proportion. The attached fluorescent group may be any fluorescer which can be chemically linked to a polymer and which has a lower energy for its singlet electronic excited state compared to the excited state of the dioxetane product. The fluorescent group enhances the chemiluminescence efficiency of the dioxetane by acting as an energy acceptor which becomes excited and releases the excitation energy in the form of light. Examples of fluorescers useful in practicing the present invention include but is not limited to any fluorescent dye; aromatic compounds including polycyclic aromatic compounds, biphenyls, terphenyls, stilbenes, heteroaromatic and polycyclic heteroaromatic compounds such as acridines, coumarins, phthalocyanines, furans, oxazoles, oxadiazoles, benzothiazoles, quinolines, xanthenes, fluorescein and fluorescein derivatives, e.g. amidofluorescein, eosin and eosin derivatives, rhodamines and resorufins.

Further, the present invention relates to a method for additionally enhancing the chemiluminescence through energy transfer to a fluorescent compound which may be chemically bound to the phosphonium salt or associated with the salt through ionic or hydrophobic interactions. Examples of fluorescers useful in practicing the present invention include but is not limited to any fluorescent dye; aromatic compounds including polycyclic aromatic compounds, biphenyls, terphenyls, stilbenes, heteroaromatic and polycyclic heteroaromatic compounds such as acridines, coumarins, phthalocyanines, furans, oxazoles, oxadiazoles, benzothiazoles, quinolines, xanthenes, fluorescein and fluorescein derivatives, e.g. amidofluorescein, eosin and eosin derivatives, rhodamines and resorufins.

Further, the present invention relates to an improved method for detecting chemiluminescence from a stable 1,2-dioxetane triggered by an activating agent selected from acids, bases, salts, enzymes, inorganic and organic catalysts and electron donors in the presence of the polyvinyl phosphonium salt enhancer. The present invention also relates to an improved method for detecting activating agents selected from acids, bases, salts, enzymes, inorganic and organic catalysts and electron donors using the polyvinyl phosphonium salt enhancer.

Further the present invention relates to a method and compositions for the detection of enzymes, in immunoassays, e.g. ELISA and the detection of enzymelinked nucleic acids, antibodies and antigens. Detection of the light emitted may be readily performed using a luminometer, X-ray film or with a camera and photographic film.

The anion of the polyvinyl phosphonium salt is preferably chloride. Other anions include azide, bromide, iodide, fluoride, sulfate, nitrate and carboxylate, all of which are preferably water soluble and non-interfering. These could be produced directly or by ion exchange.

Other polyvinyl phosphonium polymers are for instance:

1.

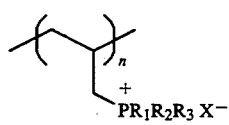

2. 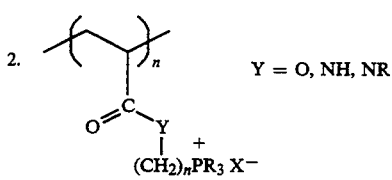 Y = O, NH, NR and copolymers with styrene or divinylbenzene.

3.

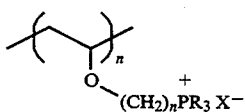

4. 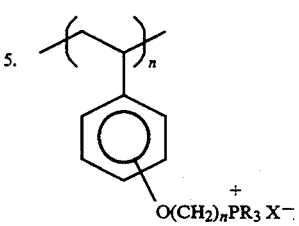

5. 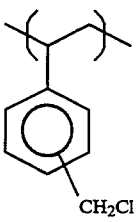

SPECIFIC DESCRIPTION

1. Synthesis of Polymeric Phosphonium Salt enhancers

All of the polymers were made via the general reaction:

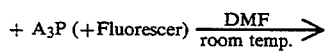

(152.62 g/mol)
mixture of meta and para

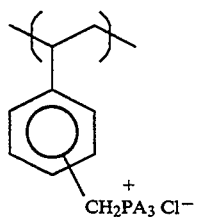

Polyvinylbenzyltrimethylphosphonium chloride (polymer TM). (M.W. of repeating unit=228.70 g/mol): 100 g of poly(vinylbenzyl chloride) (Monomer-Polymer Laboratories, Trevose, Pa.) was dissolved in anhydrous DMF (~50 mL). Once the polymer had completely dissolved, 19.7 mL (0.0197 mol, 3 equivalents based on repeating unit of starting polymer) of 1M trimethylphosphine in toluene (from Aldrich, Milwaukee, Wis.) was added to the solution. The reaction vessel was then purged with nitrogen. The reaction mixture was then allowed to stir for four days. During this time, the polymer product precipitated. The slightly yellowish white polymer solids were then filtered off and washed with ~1L of toluene. After thorough air drying, 1.41 g (94.1% yield assuming complete substitution) of off-white solid was obtained. Characterization of this polymer by NMR in $D_2O$ showed the following: $^1H$ NMR $\delta=7.0$ and 6.6 (4H), 3.6 (1.7H), and 1.7 (11.8H); $^{13}C$ NMR $\delta=130-127, 41, 31$ and 7 (doublet); $^{31}P$ NMR $\delta=27-25.5$.

Vinylbenzyltrimethylphosphonium chloride, copolymer with vinylbenzylfluorescein (polymer TM/F). (M.W. of repeating unit=228.70 g/mol); 1.00 g of poly(vinylbenzyl chloride) (from Monomer-Polymer Laboratories) was dissolved in anhydrous DMF (~50 mL) Once the polymer had completely dissolved, 10 mg of water soluble fluorescein, dye content ~70% (Aldrich) and 19.7 mL (0.0197 mol, 3 equivalents based on repeating unit of starting polymer) of 1M trimethylphosphine in toluene (Aldrich) were added to the solution. The reaction vessel was then purged with nitrogen. The reaction mixture was then allowed to stir for four days. During this time, the polymer product precipitated. The fluorescent yellow colored polymer solids were then filtered off and washed with ~1L of toluene. A fluorescent yellow solid, (1.39 g, 92.8% yield assuming complete substitution) was isolated after thorough air drying. Characterization of this polymer by NMR in $D_2O$ showed the following: $^1H$ NMR $\delta=7.0$ and 6.6 (4H), 3.6 (1.9H), and 1.7 (10.9H); $^{13}C$ NMR $\delta=130-127, 41, 31,$ and 7 (doublet); $^{31}P$ NMR $\delta=27-25.5$.

Polyvinylbenzyltributylphosphonium chloride (polymer TB). (M.W. of repeating unit=354.94 g/mol): 2.00 g of poly(vinylbenzyl chloride) (Monomer-Polymer Laboratories) was dissolved in anhydrous DMF (~100 mL). Once the polymer had completely dissolved, 15 mL (0.0602 mol, 4.6 equivalents based on repeating unit of starting polymer) of tributylphosphine (Aldrich) was added to the solution. (Only 3 equivalents of tributylphosphine are necessary to make the TB polymer.) The reaction vessel was then purged with Argon. After stirring for four days, even though no precipitate had formed the reaction was stopped and worked up. The reaction mixture was poured into a large Erlenmeyer flask and toluene was added to the stirred mixture until all of the polymer began to precipitate. The supernatant was decanted off and more toluene added; a total of ~0.5-1L of toluene was used. The mixture was stirred and the solid crushed manually until it formed a fine powder. The fine particles of polymer were then filtered off and washed with ~1L of toluene. Air drying of the polymer product yielded 4.41 g (94.8% yield assuming complete substitution) of slightly yellowish white solid (subsequent batches using poly(vinylbenzyl chloride) (Aldrich) as the starting material resulted in highly white product). Characterization of this polymer by NMR in $D_2O$ showed the following: $^1H$ NMR $\delta-7.2$ and 6.5 (4H), 3.6 (1.8H), and 2.0, 1.3, and 0.8 (29.5); $^{13}C$ NMR $\delta=130-127$, $24-22.5$, $19-17$, and $13-12.5$; $^{31}P$ NMR $\delta-33.32$.

Vinylbenzyltributylphosphonium chloride, copolymer with vinylbenzylfluorescein (polymer TB/F). (M.W. of repeating unit $-354.94$ g/mol): 2.00 g of poly(vinylbenzylchloride) (Monomer-Polymer Laboratories) was dissolved in anhydrous DMF (~125 mL). Once the polymer had completely dissolved, 20.1 mg of water soluble fluorescein, dye content ~70% (Aldrich), and 15 mL (0.060 mol, 3 equivalents based on repeating unit of starting polymer) of tributylphosphine (Aldrich) were added to the solution. The reaction vessel was then purged with argon. After stirring for four days, the reaction was stopped and worked up even though none of the polymer had precipitated. The orange reaction mixture was then poured into a large Erlenmeyer flask and 800 mL toluene was added causing an orange precipitate to form. The resulting suspension was allowed to stir for one hour before the precipitate was filtered off and washed with another 800 mL of toluene. After several hours of air drying, 3.88 g (83.4% yield assuming complete substitution) of fluorescent yellow solid (slightly darker yellow in appearance than TMF) was obtained. Characterization of this polymer by NMR in $D_2O$ showed the following: $^1H$ NMR $\delta=7.2$ and 6.5 (4H), 3.6 (1.8H), and 2.0, 1.3, and 0.8 (31.7); $^{13}C$ NMR $\delta=130-127$, $24-22.5$, $19-17$, and $13-12.5$; $^{31}P$ NMR $\delta=33.5-32$.

Vinylbenzyltributylphosphonium chloride, copolymer with vinylbenzyl-Rose Bengal (polymer TB/RB). (M.W. of repeating unit $-354.94$ g/mol): 1.00 g of poly(vinylbenzyl chloride) (Aldrich) was dissolved in ~50 mL of anhydrous THF. Once the polymer had completely dissolved, 50.1 mg of Rose Bengal, disodium salt (Aldrich) was added to the solution. The reaction vessel was then purged with nitrogen. Another 50 mL of anhydrous THF was added via syringe to dissolve most of the Rose Bengal. Tributylphosphine, 5 mL (0.020 mol, 3 equivalents based upon the repeating unit of the starting polymer) was then added via syringe. The reaction mixture was purged with nitrogen and left to stir. After stirring for seven days, the reaction was stopped and worked up. The now colorless THF solution was then poured away from the red solid which had precipitated out of the THF and coated the walls of the reaction vessel. The polymer was then washed several times with THF and dried in vacuo giving a glassy red solid. At this point, the polymer showed strong red fluorescence in water (Rose Bengal is not fluorescent in water) and to give red chemiluminescence when a solution of the polymer and dioxetane 1 was triggered by alkaline phosphatase in pH 9.6 buffer. The polymer was dissolved in dichloromethane and the solvents were then removed in vacuo (first on the rotovap and then under high vacuum with heating). The $^1H$ NMR spectrum of the polymer indicated THF was still present, so the sample was dried further until only a trace amount of THF was still visible by $^1H$ NMR. A yield of 168 g (72.4% yield assuming complete substitution) of TB/RB was obtained. The polymer was then characterized by NMR in $D_2O$ showing the following: $^1H$ NMR $\delta=7.2$ and 6.5 (4H), and 2.0, 1.4, and 0.8 (29.3H); $^{13}C$ NMR $\delta=130-127$, $24-22.5$ $19-17$, and $13-12.5$; $^{31}P$ NMR $\delta=33-32$.

PolyvinylbenzyltrioctylphosPhonium chloride (polymer TO). (M.W. of repeating unit=523.25 g/mol): 2.00 g of poly(vinylbenzyl chloride) (Monomer-Polymer Laboratories) was dissolved in ~50 mL of anhydrous THF under argon. Once the polymer completely dissolved, 15.9 g (0.0429 mol, 3.3 equivalents based upon the repeating unit of the starting polymer) of tri-(n-octyl)-phosphine was added via syringe. The solution was then left stirring under argon. After six days of stirring, the reaction was stopped and worked up. The reaction mixture was poured into a large Erlenmeyer flask and ~1L of toluene was added. This had no effect, so all but ~100 mL of the solvents were removed in vacuo. ~1L of hexanes were then added to the resulting solution precipitating the polymer. The polymer was then isolated by filtration and after air drying still smelled of phosphine. It was therefore redissolved in THF and precipitated with hexanes. After thorough air drying, 378 g (55.1% yield assuming complete substitution) of slightly yellowish white solid was obtained. Characterization of this polymer by NMR in $CDCl_3$ showed the following: $^1H$ NMR $\delta=7.1$ and 6.4 (4H), 4.4 (1.6H), and 2.3, 1.3 and 0.8 (39.5H); $^{31}P$ NMR $\delta=32.5-31.5$.

Polyvinylbenzyltrioctylphosphonium chloride, copolymer with polyvinylbenzyltributylphosphonium chloride (polymer 3TB/TO). Poly(vinylbenzyl chloride) (Aldrich, 2.01 g) was dissolved in 10 mL of anhydrous DMF. Once the polymer was completely dissolved, 1.23 g (0.00332 mol, 0.25 equivalents based upon repeating unit of the starting polymer) of tri-n-octyl-phosphine was added to the solution. The reaction vessel was then flushed with argon and left stirring. After stirring for two days, 9.5 mL (0.038 mol, 2.9 equivalents based upon repeating unit of the starting polymer) of tributylphosphine was added to the reaction mixture via syringe. After another two days of stirring, the reaction was stopped and worked up. The reaction mixture was poured into a large Erlenmeyer flask and ~1L of toluene was added Once the polymer was manipulated to a fine suspension of particles in the toluene, it was filtered off and washed with ~500 mL of toluene. After thorough air drying, 4.31 g (82.8% yield assuming complete substitution and complete consumption of the trioctylphosphine) of white solid was obtained. Characterization of this polymer by NMR in $D_2O$ showed the following: $^1H$ NMR $\delta=7.2$ and 6.5 (4H), 3.6 (1.5H), and 2.0, 1.4 and 0.8 (43.1 H); $^{13}C$ NMR $\delta=130-127$, 24−22.5, 19−17, and 13−12.5. Other mixed TO and TB polymers were synthesized using similar methods.

2. Measurement of Chemiluminescence Kinetics and Quantum Yields

Chemiluminescence intensities and rate measurements were performed using either a Turner Designs (Sunnyvale, Calif.) model TD-20e luminometer or a Labsystems Luminoskan luminometer (Helsinki, Finland). Temperature control of samples analyzed in the Turner luminometer was achieved by means of a circulating water bath connected to the instrument. Quantitative measurement of light intensities on the Turner luminometer was extended beyond the $10^4$ linear range of the detector by a neutral density filter. Data collection was controlled by an Apple MacIntosh SE/30 computer using the LumiSoft TM data reduction program (Lumigen, Inc. Detroit, Mich.).

3. Chemiluminescence and Fluorescence Spectra

Chemiluminescence and fluorescence spectra were measured using a Fluorolog II fluorimeter (Spex Ind., Edison, N.J.) with 1 cm quartz cuvettes. All measurements were performed at ambient temperature. A solution of 2 mL of Lumigen® PPD in 221 buffer (0.2 M, pH 9.6) containing 0.88 mM $MgCl_2$ and 0.1% enhancer TB was placed in a cuvette and chemiluminescence initiated by injection of 5 μL of a solution of alkaline phosphatase (Biozyme Laboratories, San Diego, Calif.). The spectrum was scanned when the light intensity reached a constant level. FIG. 1 shows a comparison of the chemiluminescence spectra obtained under these conditions with that obtained from Lumi-Phos® 480, a commercial formulation of the same dioxetane containing the surfactant CTAB (Lumigen, Inc., Detroit, Mich.). The spectra are normalized for presentation.

Figure 2:
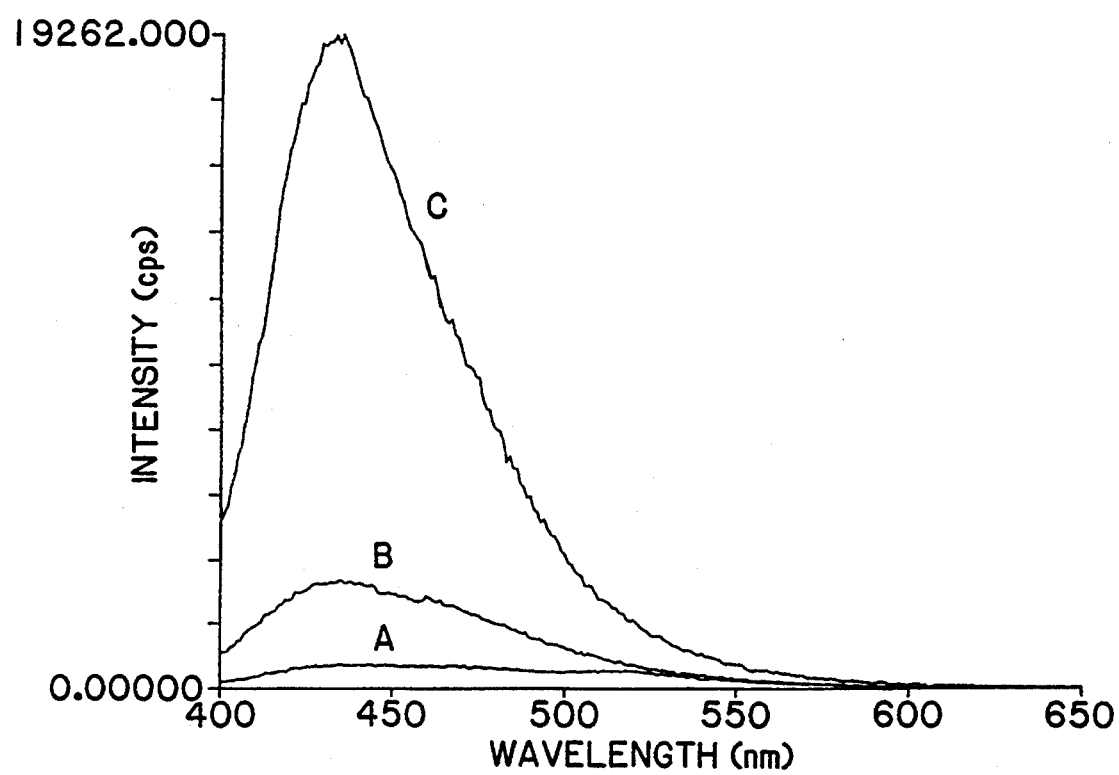
FIG. 2 is a graph showing a comparison of the fluorescence spectra of methyl 3-hydroxybenzoate in alkaline solution in the presence of enhancers of the present invention and in the commercial reagent LUMI-PHOS® 480. The graph shows methyl 3-hydroxybenzoate in (a) 0.75 M 2-methyl-2-amino-1-propanol buffer, pH 9.6 containing 1.1 mM CTAB (as found in Lumi-Phos® 480), (b) 0.2 M 2-methyl-2-amino-1-propanol buffer, pH 9.6 containing 0.5 mg/mL TB and (c) 0.2 M 2-methyl-2-amino-1-propanol buffer, pH 9.6 containing 0.5 mg/mL 18TB/TO. The fluorescence of methyl 3-hydroxybenzoate in 221 buffer containing CTAB was not affected by varying the concentration of buffer from 0.75 M to 0.2 M.

Fluorescence spectra of the reaction product of the dioxetane, methyl 3-hydroxybenzoate, in alkaline buffer solution show that the fluorescence is greatly increased in the presence of the polyvinyl phosphonium salts. The largest enhancement of fluorescence quantum yield of the ester decomposition product occurs in the presence of polymer 3TB/TO bearing tributyl- and trioctylphosphonium groups (FIG. 2). It is observed that the fluorescence spectra are blue-shifted compared to the chemiluminescence spectra (FIG. 1).

4. Determination of Optimum Enhancer Concentration in Enzyme Assay

Figure 3:
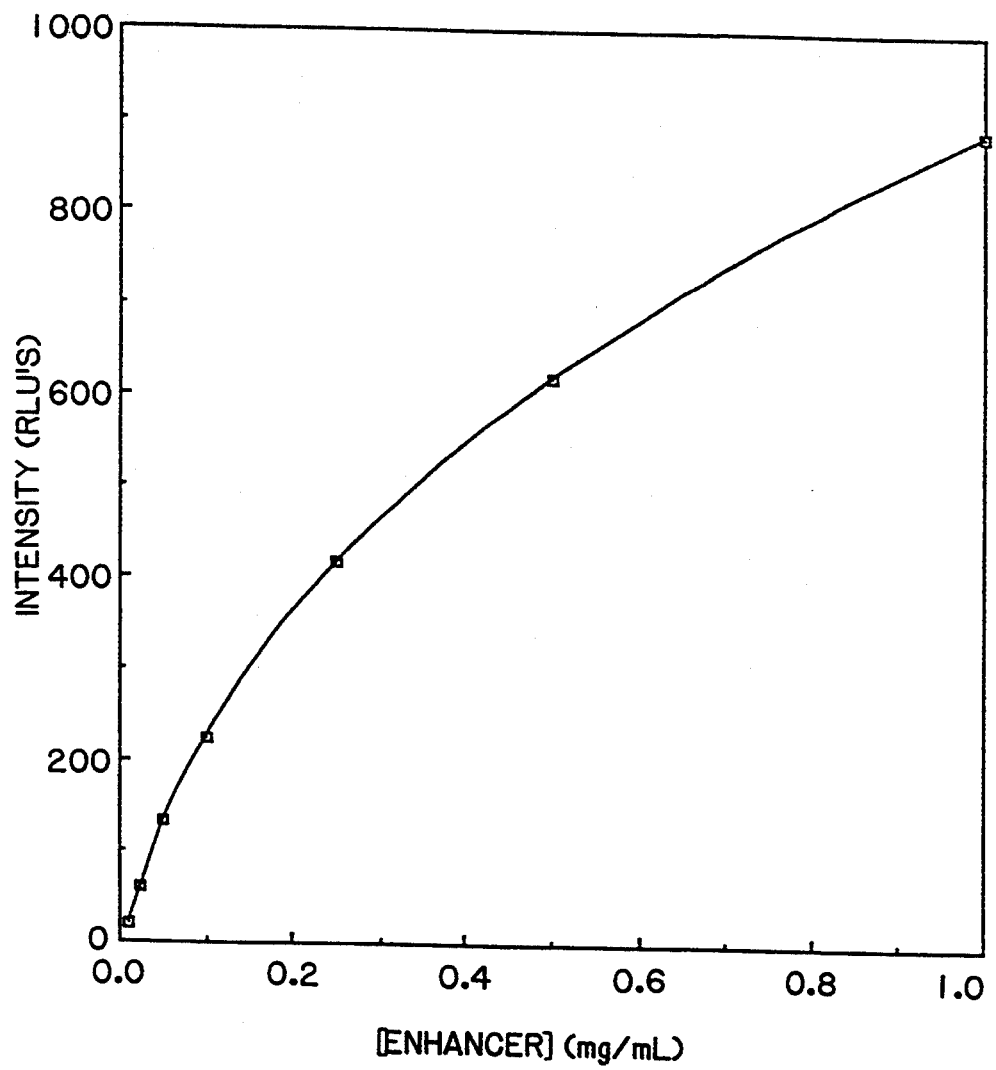
FIG. 3 is a graph showing the light intensity as a function of enhancer concentration with an alkaline phosphatase triggered 1,2-dioxetane. The graph shows intensity from 100 $\mu$L of a 0.33 mM solution of Lumigen® PPD in 0.2 M 221 buffer, pH 9.6 containing 0.88 mM $MgCl_2$ and various concentrations of 3TB/TO in the range of 1.0 to 0.01 mg/mL. The chemiluminescent reaction was initiated by addition of $5.5 \times 10^{-18}$ mol of calf intestinal alkaline phosphatase at 37° C. Values shown are the average of triplicate results.
Figure 4:
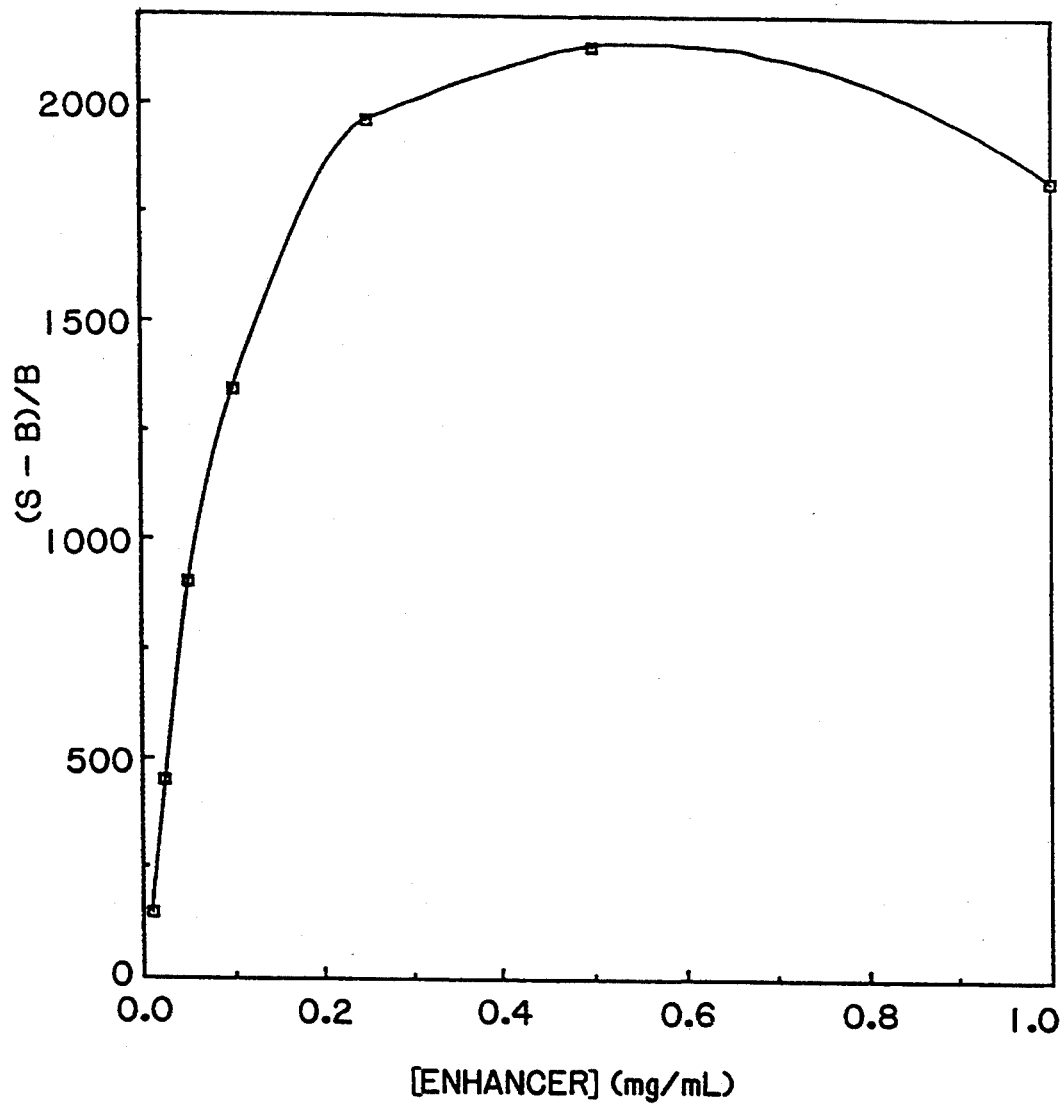
FIG. 4 is a graph showing light intensity compared to background versus amount of enhancer with an alkaline phosphatase triggered 1,2-dioxetane. The graph shows the ratio of chemiluminescence intensity (S) to reagent background (B) as a function of the optimum concentration of 3TB/TO in the chemiluminescent decomposition of Lumigen® PPD by alkaline phosphatase at 37° C. in 0.2 M 221 buffer, pH 9.6 containing 0.88 mM $MgCl_2$. Values shown are the average of triplicate results. The optimum signal/background was obtained at an enhancer concentration of 0.5 Mg/mL.

To each of three wells in a 96-well microplate was added 100 μL of a 0.33 mM solution of dioxetane 1 in 0.2 M 2-methyl-2-amino-1-propanol (221) buffer, pH 9.6 with 0.88 mM $MgCl_2$ and various concentrations of enhancer 3TB/TO in the range of 1.0 to 0.01 mg/mL. The plate was incubated at 37° C. and chemiluminescence emission initiated by addition of $5.5 \times 10^{-18}$ mol of calf intestinal alkaline phosphatase. Luminescence was measured for two hours in a Luminoskan luminometer. Maximum luminescence intensity values shown are the average of triplicate results, corrected for the luminescence from appropriate blank solutions without enzyme (FIG. 3). Light intensity increases monotonically over this range but the optimum signal/background was obtained at an enhancer concentration of 0.5 mg/mL (FIG. 4).

5. Linearity of Detection of Alkaline Phosphatase with Lumigen® PPD+Enhancer

Figure 5:
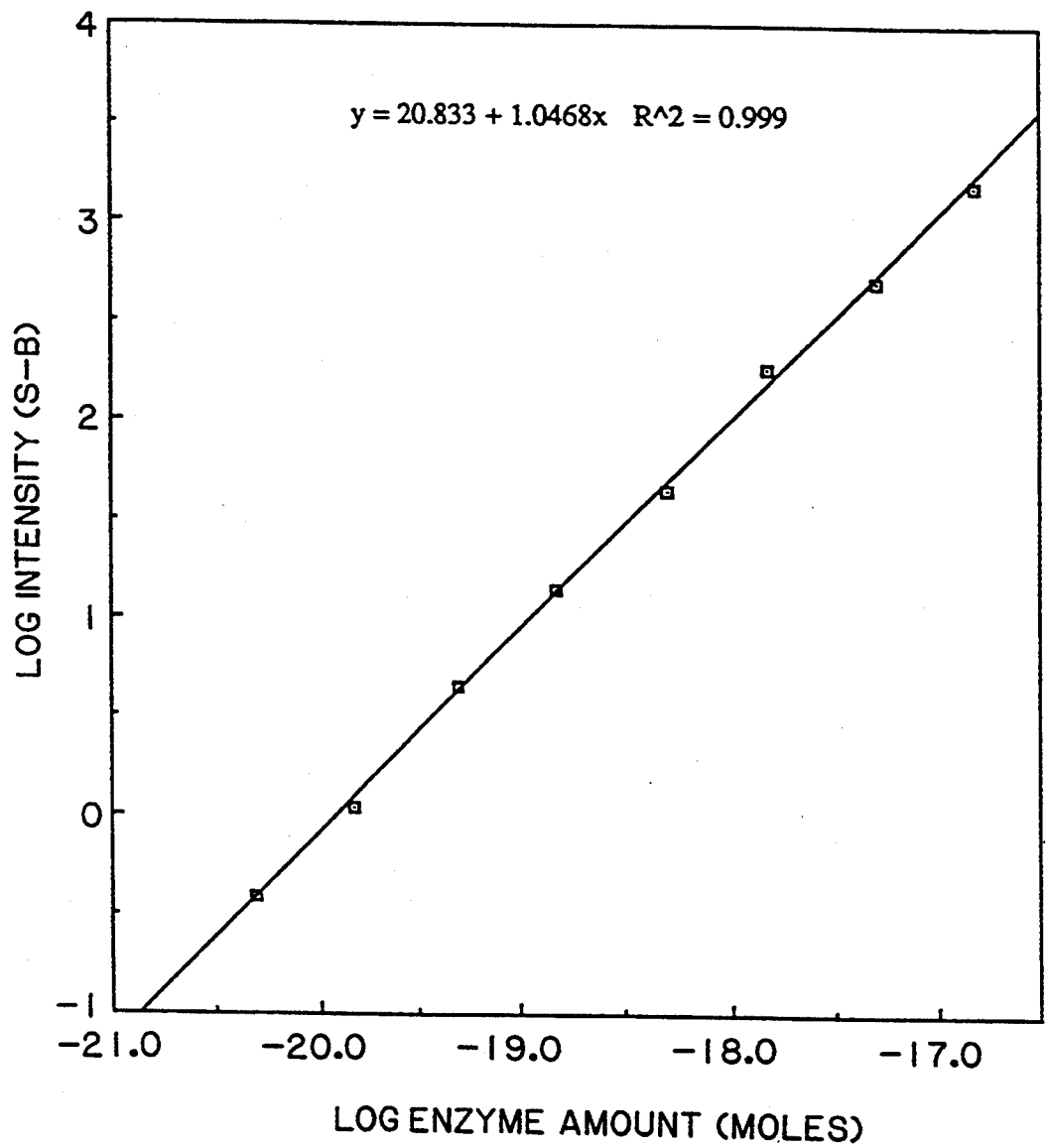
FIG. 5 is a log-log graph showing light intensity versus enzyme concentration showing that 0.005 amole of alkaline phosphatase can be detected. The graph shows dependence of maximum chemiluminescence intensity on amount of alkaline phosphatase in the chemiluminescent decomposition of Lumigen® PPD at 37° C. in 0.2 M 221 buffer, pH 9.6 with 0.88 mM $MgCl_2$ and 0.5 mg/mL 3TB/TO. The light intensity is linearly related to the amounts of enzyme between $5 \times 10^{-17}$ mol and $5 \times 10^{-21}$ mol. The limit of detection (0.005 amol of alkaline phosphatase) is 0.2000-fold lower than the limit of detection of alkaline phosphatase without using enhancer. The time to obtain maximum chemiluminescence intensity is independent of amount of enzyme over this range.

To each of six wells in a 96-well microplate was added 100 μL of a 0.33 mM solution of dioxetane 1 in 0.2 M 2-methyl-2-amino-1-propanol (221) buffer, pH 9.6 with 0.88 mM $MgCl_2$ and 0.5 mg/mL enhancer 3TB/TO. The plate was incubated at 37° C. and chemiluminescence emission initiated by addition of 5 μL of dilutions of calf intestinal alkaline phosphatase containing between $1.1 \times 10^{-17}$ mol/μL and $1.1 \times 10^{-21}$ mol/μL. FIG. 5 shows that 0.005 amol of alkaline phosphatase can be detected. This represents a 2000-fold lowering of the limit of detection compared to the same system without enhancer (data not shown). The time to maximum chemiluminescence intensity is independent of amount of enzyme over this range.

6. Comparison of Chemiluminescence Intensities-Kinetic Profile

Figure 6:
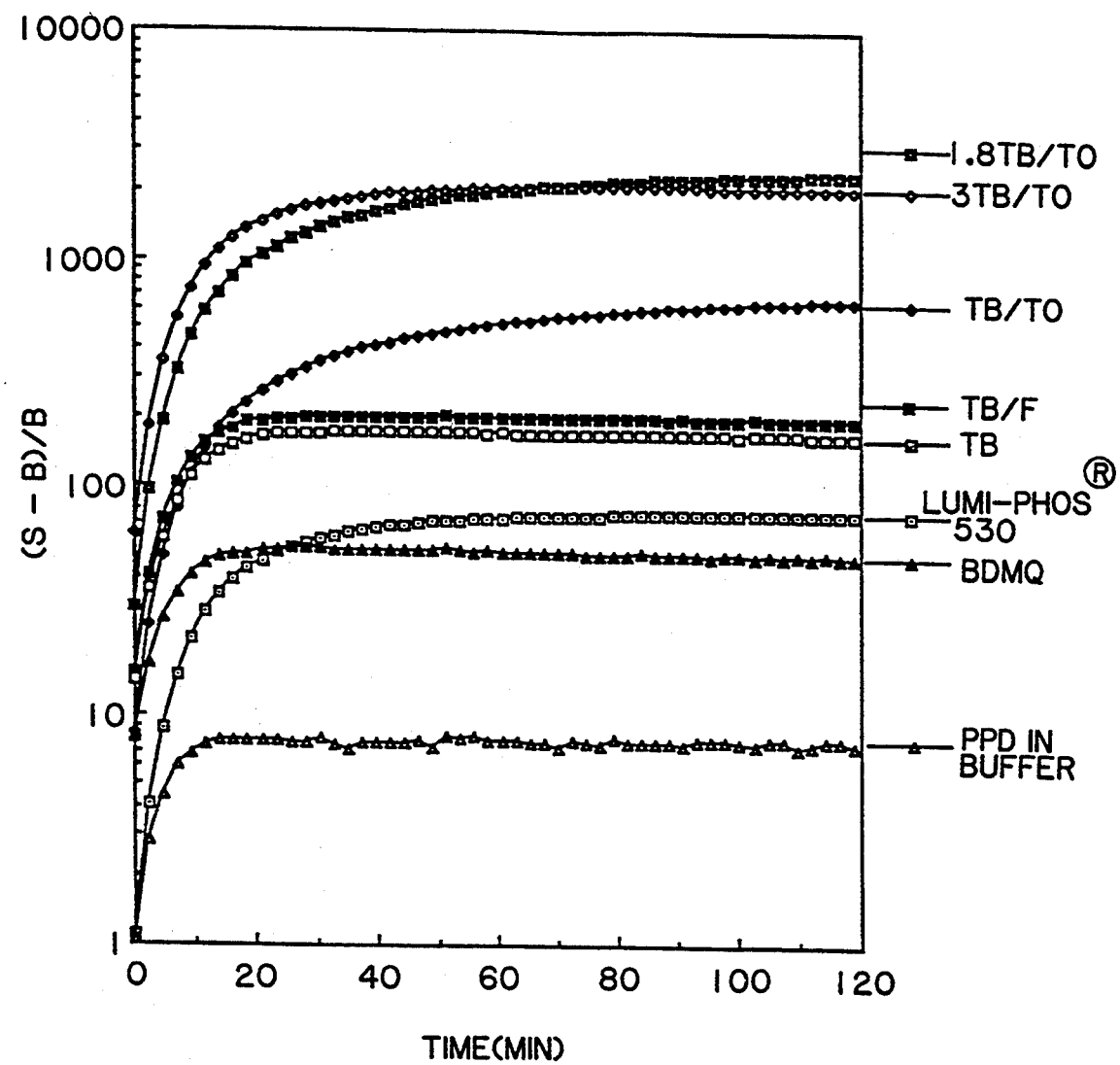
FIGS. 6 and 7 are graphs of light intensity versus time showing the effect of various enhancers and no enhancer at 5 attamoles of alkaline phosphatase. The graph of FIG. 6 shows a comparison of the signal/background ratio in the chemiluminescent assay of alkaline phosphatase. Chemiluminescence intensities from 100 $\mu$L of solutions containing various enhancers and Lumigen® PPD in 0.2 M 221 buffer, pH 9.6 triggered at 37° C. by addition of $5.5 \times 10^{-18}$ mol of calf intestinal alkaline phosphatase. Also included for comparison are: a solution with a polymeric ammonium salt (BDMQ), a solution without enhancer and the commercial reagent Lumi-Phos® 530. The graph of FIG. 7 shows a comparison of the chemiluminescence intensities from 100 $\mu$L of solutions containing enhancers of the present invention and dioxetane 1 in 2-methyl-2-amino-1-propanol (221) buffer, pH 9.6 triggered at 37° C. by addition of $5.5 \times 10^{-18}$ mol of calf intestinal alkaline phosphatase. Also included for comparison are: a solution with a polymeric ammonium salt (BDMQ), a solution without enhancer and the commercial reagent Lumi-Phos® 530.
Figure 7:
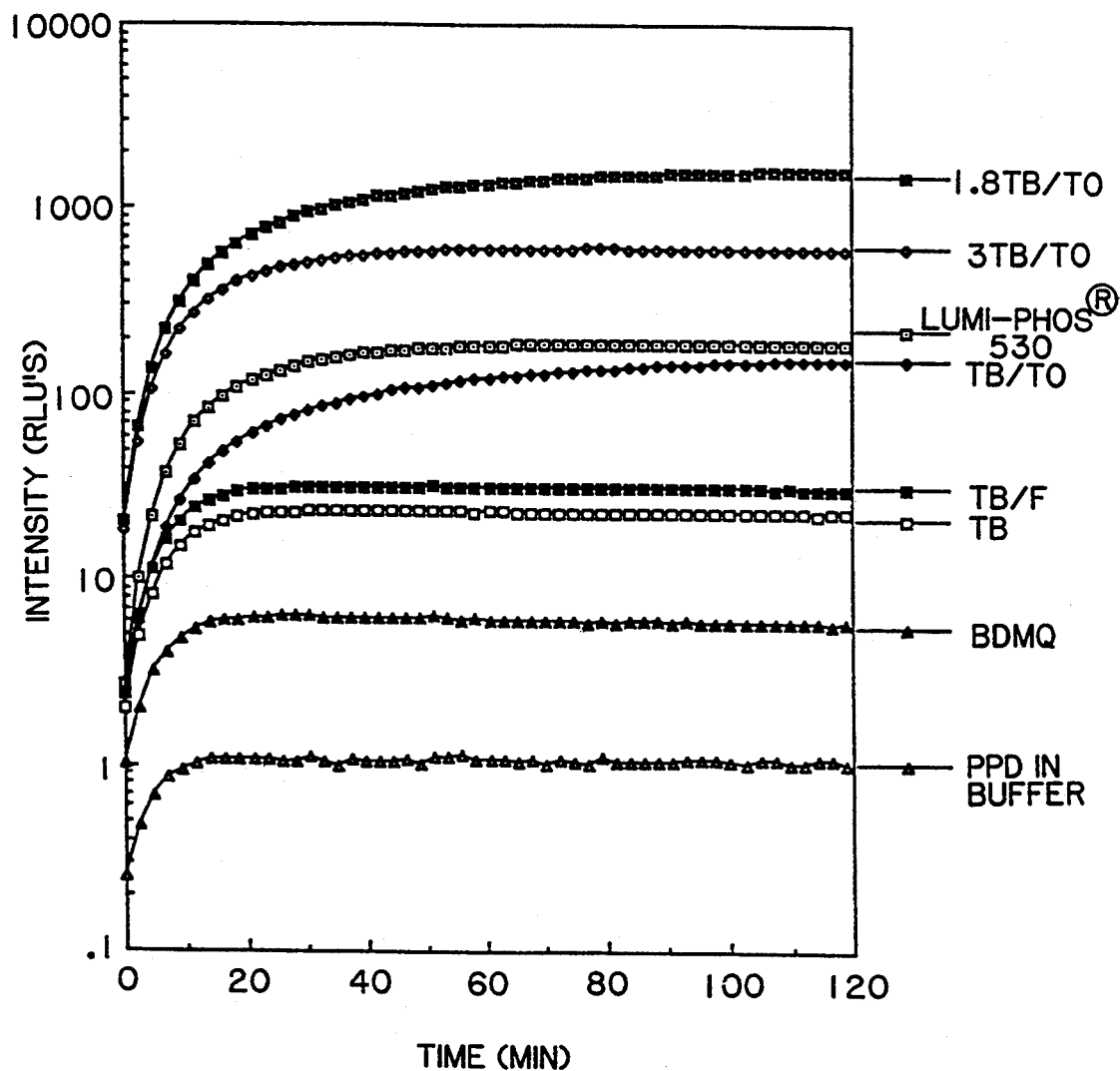

The advantage of enhancers of the present invention is shown in FIGS. 6 and 7 by a comparison of the chemiluminescence intensities from 100 μL of solutions containing enhancers of the present invention and dioxetane 1 in 2-methyl-2-amino-1-propanol (221) buffer, pH 9.6 triggered at 37° C. by addition of $5.5 \times 10^{-18}$ mol of calf intestinal alkaline phosphatase.

Addition of enhancer at a concentration of 0.5 mg/mL substantially increases the chemiluminescence intensity compared to the same solution without enhancer or to solutions containing enhancers known in the art. It will be appreciated that modification to the signal/background ratio and, in some cases, the rate of rise to maximum light intensity can be easily accomplished by varying the concentration of enhancer.

7. Enhancement of the Chemically Triggered Decomposition of Dioxetane 5

Table 1 compares the maximum chemiluminescence intensity produced by the decomposition of dioxetane 5 (10 μL of a 100 μg/mL solution in 2-propanol) when triggered at room temperature by addition of 100 μL of a 0.05 M solution of sodium hydroxide in water containing 0.5 mg/mL enhancer. Luminescence was measured for up to one hour in a Turner TD-20e luminometer. Enhancement factor is the ratio to the value obtained in the absence of any enhancer. Values shown are the average of triplicate results, corrected for the luminescence from appropriate blank solutions. The half-life ($t_{\frac{1}{2}}$) is the time required for the decay of the luminescent signal to one-half its initial value.

TABLE 1

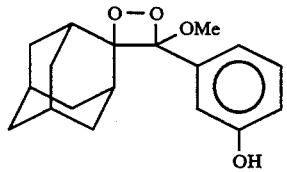

5

Enhancement of Chemiluminescence from Sodium Hydroxide-Triggering of Dioxetane 5.

| Enhancer | t 1/2 (min) | total light (Rel. Light Units) | Enhancement Factor |
|---|---|---|---|
| TB/TO[1] | 8.5 | 2.84E+06 | 852.85 |
| TO[2] | 12.7 | 2.82E+06 | 846.85 |
| 1.8TB/TO[3] | 7.2 | 2.02E+06 | 606.61 |
| 3TB/TO[4] | 4.7 | 1.28E+06 | 384.38 |
| Lumi-Phos ®530[5] | 16.7 | 1.23E+06 | 369.37 |
| TB/F[6] | 4.7 | 3.06E+05 | 91.89 |
| TB[7] | 5.2 | 1.98E+05 | 59.46 |
| TB/RB[8] | 6.3 | 1.01E+05 | 30.33 |
| BDMQ[9] | 3.3 | 4.27E+04 | 12.83 |
| TM/F[10] | 3.2 | 3.84E+04 | 11.53 |
| Lumi-Phos ®480[11] | 13.8 | 1.13E+04 | 3.39 |
| TM[12] | 3.7 | 1.01E+04 | 3.03 |
| TMQ[13] | 3.5 | 7.45E+03 | 2.24 |

TABLE 1-continued

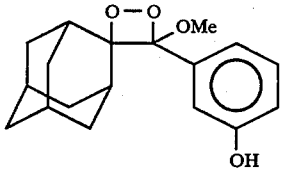

Enhancement of Chemiluminescence from Sodium Hydroxide-Triggering of Dioxetane 5.

| Enhancer | t 1/2 (min) | total light (Rel. Light Units) | Enhancement Factor |
|---|---|---|---|
| None | 2.2 | 3.33E+03 | 1.00 |

[1] Polyvinylbenzyltrialkylphosphonium chloride, 50% trioctyl, 50% tributyl.
[2] Polyvinylbenzyltrioctylphosphonium chloride.
[3] Polyvinylbenzyltrialkylphosphonium chloride, 35% trioctyl, 65% tributyl.
[4] Polyvinylbenzyltrialkylphosphonium chloride, 25% trioctyl, 75% tributyl.
[5] CTAB and N-tetradecanoylaminofluorescein contained in the commercial product of LumiPhos ®530 of Lumigen, Inc., Detroit, MI.
[6] Polyvinylbenzyltributylphosphonium chloride including covalently attached fluorescein.
[7] Polyvinylbenzyltributylphosphonium chloride.
[8] Polyvinylbenzyltributylphosphonium chloride including covalently attached Rose Bengal.
[9] Polyvinylbenzylbenzyldimethylammonium chloride. See UK Patent Application No. 89113627.7. This material was prepared using similar procedures as for TB.
[10] Polyvinylbenzyltrimethylphosphonium chloride including covalently attached fluorescein.
[11] CTAB contained in the commercial product Lumi-Phos ®480 of Lumigen, Inc., Detroit, MI.
[12] Polyvinylbenzyltrimethylphosphonium chloride.
[13] Polyvinylbenzyltrimethylammonium chloride. See UK patent Application No. 89113627.7. This material was prepared using similar procedures as for TB.

8. Enhancement of the Enzymatically Triggered Decomposition of Dioxetane 1

Table 2 compares the maximum chemiluminescence intensity produced by the decomposition of 100 μL of a 0.33 mM solution of dioxetane 1 in 0.2 M 221 buffer, pH 9.6, 0.88 mM $MgCl_2$ plus 0.5 mg/mL enhancer when triggered at 37° C. by addition of 5 amol of alkaline phosphatase in water. Luminescence was measured for two hours in a Luminoskan ™ luminometer and the maximum light intensity recorded. Values shown are the average of triplicate results. Background intensity is the light level in the absence of enzyme. The value of $I_{\frac{1}{2}}$ represents the time required to reach one-half of the maximum light intensity. The value of $I_{BG}$ represents the light intensity in the absence of enzyme. The term (S-B)/B is the ratio of the corrected maximum light intensity to the background light intensity. The polymers of the present invention can also be used to enhance the chemiluminescence of phosphate substituted dioxetanes related to dioxetane wherein the adamantyl group is substituted with hetero atom containing groups such as 5-chloro.

TABLE 2

Enhancement of Chemiluminescence from Alkaline Phosphatase-Triggering of Dioxetane 1.

| Enhancer | Time to $I_{\frac{1}{2}}$(min) | $I_{max}$(S) | $I_{BG}$(B) | (S—B)/B |
|---|---|---|---|---|
| 1.8TB/TO | 24 | 1600 | 0.69 | 2320 |
| 3TB/TO | 12 | 613 | 0.30 | 2060 |
| TB/TO | 28 | 155 | 0.24 | 660 |
| Lumi-Phos 530 | 16 | 190 | 2.47 | 75 |
| TB/F | 7 | 32 | 0.16 | 203 |
| TB | 7 | 23 | 0.13 | 170 |
| BDMQ | 5 | 6.2 | 0.12 | 53 |
| None | 3 | 1.1 | 0.12 | 8 |

9. Application of Enhancers to the Chemiluminescent Detection of Protein by Western blotting The advantage of compositions of the present invention for the chemiluminescent detection of proteins by the technique of Western blotting is demonstrated in the following example. Similar enhancements are observed for detection of DNA on membranes such as nylon.

Western Blot - Comparison to Commercial Chemiluminescent Alkaline Phosphatase Detection Reagents.

Reagents

Rabbit ant-goat IgG-alkaline phosphatase conjugate was obtained from Cappel Products (Durham, N.C.). Human transferrin and fractionated goat ant-human transferrin serum were purchased from Sigma Chemical Co (St. Louis, Mo.). The IgG sample was centrifuged at 10,000 g for two minutes and the supernatant was used in the immunological reaction. Immobilon-P transfer membrane was obtained from Millipore Corp. (Bedford, Mass.) Kodak X-OMAT-AR and OMC (Rochester, N.Y.) films were used in the assay procedure.

Sodium dodecyl sulfate-polyacrylamide gel electrophoresis (SDS-PAGE) and immunoblot analysis.

SDS-PAGE was performed utilizing the buffer system described by Laemmli (U.K. Laemmli, Nature (London), 227,680 (1970)). The stacking gel was 4.38% acrylamide: 0.12% bisacrylamide. The separating gel was 6.81% acrylamide: 0.19% bisacrylamide. Following electrophoresis, the gel was equilibrated for 7-8 minutes with the transfer buffer which contained 20 mM Tris, 153 mM glycine and 20% (v/v) methanol. The gel, sandwiched between a sheet of transfer membrane and a sheet of chromatography paper 3MM (Whatman), was placed in the transfer unit (Bio-Rad Laboratories, Richmond, Calif.). The proteins in the gel were electroeluted for 50-60 minutes at 4° C. at a 100 V constant voltage. The membrane was then placed in 50 mM Tris-HCl buffered saline at pH 7.4 (TBS) at 4° C. overnight. After this period the membrane was washed with TBS for 15 minutes.

The membrane was treated with 0.05% Tween-20 in 50 mM Tris-HCl buffered saline at pH 7.4 (T-TBS) containing 1% non-fat powdered milk (NFM) for one hour at room temperature. This blocked membrane was incubated for 75 minutes at room temperature with primary antibody (1:500 dilution of goat anti-human transferrin IgG fraction) using T-TBS containing 1% NFM. The membrane was then rinsed and washed three times for ten minutes each with T-TBS at room temperature. The washed membrane was incubated for one hour at room temperature with secondary antibody (1:5000 dilution of rabbit anti-goat IgG-alkaline phosphatase conjugate) using T-TBS containing 1% NFM. The membrane was rinsed and washed four times for ten minutes each with T-TBS followed by a ten minute wash with TBS. The washed membrane was soaked in one of four detection reagents (A-D) for five minutes, drained and placed between sheets of transparency film. The X-ray film was exposed to the membrane for ten to 30 seconds and developed.

Chemiluminescent detection of Western blotted human transferrin utilizing Lumi-Phos ® 530 (A) another reagent containing BDMQ (B) and two other reagents using enhancers of this invention (C,D) was performed on two different x-ray films. The composition of the detection reagent solutions was as follows:

| | A | B | C | D |
|---|---|---|---|---|
| [Dioxetane 1] | 0.33 mM | 0.66 mM | 0.66 mM | 0.66 mM |
| Buffer | 221,0.75M | 221,0.2M | 221,0.2M | 221,0.2M |
| pH | 9.6 | 10.1 | 10.1 | 10.1 |
| [$Mg^{2+}$] | 0.88 mM | 0 | 0.88 mM | 0.88 mM |
| [$NaN_3$] | 0 | 0.1% | 0 | 0 |
| Enhancer | CTAB, | BDMQ | TB/F,0.1% | TB,0.1% |

-continued

| A | B | C | D |
|---|---|---|---|
| 1.1 mM F1-S, 37μM | 0.1% | | |

Figure 8A:
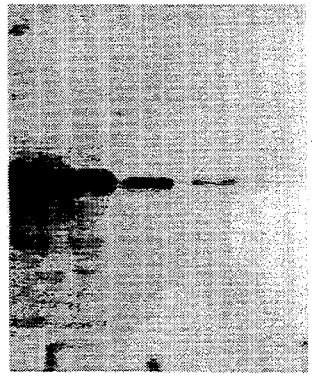
FIGS. 8A and 8B show the result of a Western blot analysis of human transferrin with chemiluminescent detection using an alkaline phosphatase-triggered 1,2-dioxetane in the presence of enhancer. Shown is Western blotted human transferrin utilizing Reagent C (FIG. 8A) and Reagent D (FIG. 8B). Human transferrin loaded into each slot was (1) 1000 pg, (2) 200 pg, (3) 50 pg, (4) 20 pg and (5) 5 pg. The blots were exposed to Kodak X-OMAT AR film for 30 seconds after a 30 minute incubation in their respective detection reagent. Only faint bands for slots 1 and 2 were visible using detection reagents A and B.
Figure 8B:

To determine the sensitivity of these detection systems for Western blotting, a model system of transferrin was utilized to provide polypeptide bands in known quantities. The transferrin standards utilized were detectable down to 5 pg/slot after a 20 second exposure to OMC X-ray film utilizing reagent C (FIG. 8A) and reagent D (FIG. 8B). However, for a 20 second exposure, only faint bands representing one nanogram and five nanograms of transferrin/slot were observed when reagent A and reagent B were used for detection. Exposure times in excess of seven minutes were required to detect 5 pg/slot of transferrin with reagents A or B. The signal to background ratios for detection of 5 pg/slot transferrin were similar among the four systems, though the exposure times were significantly different. Membranes treated with reagents C and D using enhancers of the present invention achieved equivalent signal levels on exposure to X-ray film 15 times faster than membranes treated with reagents A and B.

The speed advantage of reagents C and D was even more pronounced when the commonly used X-OMAT AR X-ray film was utilized for detection. For equivalent signal levels, reagents A and B required significantly longer exposure times.

10. Enhancement in Non-aqueous and Mixed Solvent Solutions

Chemiluminescence from the base-triggered decomposition of dioxetane 5 is also enhanced by polymeric phosphonium salts of the present invention in solutions wherein water is not the only solvent. Triggering of 100 μL of a 10 μg/mL solution of dioxetane 5 in water/methanol or methanol in a Turner luminometer with 100 μL of 0.05 M KOH in methanol produced chemiluminescence which was enhanced in the presence of 0.25 mg/mL of polymer 3TB/TO.

TABLE 3

Enhancement of Chemiluminescence from Base-Triggering of Dioxetane 5 in Alcohol and Alcohol/Water Solvent by Polymer 3TB/TO.

| | 50% Water/50% Methanol | | 100% Methanol | |
|---|---|---|---|---|
| | Without Enhancer | With Enhancer | Without Enhancer | With Enhancer |
| $I_{max}$ | 230 | 3000 | 57 | 80 |
| | 236 | 2700 | 58 | 70 |
| | 250 | 2530 | 60 | 79 |
| Avg. | 239 | 2743 | 58 | 76 |

TABLE 3-continued

Enhancement of Chemiluminescence from Base-Triggering of Dioxetane 5 in Alcohol and Alcohol/Water Solvent by Polymer 3TB/TO.

| | 50% Water/50% Methanol | | 100% Methanol | |
|---|---|---|---|---|
| | Without Enhancer | With Enhancer | Without Enhancer | With Enhancer |
| Enhancement | | 11.6 | | 1.3 |

11. Enhancement of the Enzymatically Triggerred Decomposition of a Galactoside-Protected Dioxetane Table 4 compares the total chemiluminescence intensity produced by the enzymatic decomposition and subsequent base-triggering of the galactoside-protected dioxetane Lumigen ® GPD. The sample was prepared by incubating 100 μL of a 100 μg/mL solution of the galactoside-protected dioxetane Lumigen ® GPD in 0.1 M phosphate buffer, pH 7.5, 0.88 mM $MgCl_2$ with 5 μl of a 5 μg/ml solution of β-galactosidase-streptavidin in water. The chemiluminescence was triggered at 37° C. by addition of 100 μL of 0.05 M NaOH containing 0.5 mg/mL enhancer. Luminescence was measured for 30 minutes in a Turner luminometer and the total light intensity recorded. Background intensity is the total light intensity of an identical sample incubated without enzyme. The value of $I_{BG}$ represents the light intensity in the absence of enzyme. The term (S-B)/B is the ratio of the corrected maximum light intensity to the background light intensity.

TABLE 4

Enhancement of Chemiluminescence from β-Galactosidase-Triggering of Lumigen ® GPD.

| Enhancer | $I_{max}(S)$ | $I_{BG}(B)$ | (S—B)/B |
|---|---|---|---|
| 3TB/TO | 1.05e + 07 | 4.43e + 04 | 235 |
| None | 1.49e + 05 | 1.06e + 03 | 140 |

I claim:
1. A polyvinylLinktriAylphosphonium and fluorescent group containing polymer wherein Link is a linking group between the polymer and the phosphonium cation containing 1 to 20 carbon atoms and A is selected from the group consisting of alkyl containing 1 to 20 carbon atoms or alkyl and aralkyl groups each containing 1 to 20 carbon atoms and wherein the fluorescent group is attached to the polymer.

2. The polymer of claim 1 wherein the fuorescent group is selected from the group consisting of fluorescein and Rose Bengal.

3. The polymer of claim 2 wherein Link is benzyl.

4. The polymer of claim 2 wherein the LinktriAyl phosphonium is benzyltrimethylphosphonium or benzyltributylphosphonium.

5. The polymer of claim 1 wherein Link is a benzyl group, wherein A is a methyl group and wherein the fluorescent group is a fluorescein group.

6. The polymer of claim 1 wherein Link is a benzyl group, wherein A is a butyl group and wherein the fluorescent group is a fluorescein group.

* * * * *

UNITED STATES PATENT AND TRADEMARK OFFICE
CERTIFICATE OF CORRECTION

PATENT NO. : 5,431,845
DATED : July 11, 1995
INVENTOR(S) : Hashem Akhavan-Tafti

It is certified that error appears in the above—identified patent and that said Letters Patent is hereby corrected as shown below:

Column 6, line 30, "0.2000-fold" should read --2000-fold--.

Column 8, line 15, the structure " 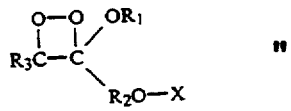 "

should read as follows: -- 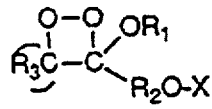 --.

Column 8, line 67, "salts" should be --salt--.

Column 11, line 67, "polyvinyl. phosphonium" should read --polyvinyl phosphonium--.

Column 16, line 15, a comma --,-- should be inserted after "22.5".

Column 16, line 20, "Polyvinylbenzyltrioctylphos Phonium" should read --Polyvinylbenzyltrioctylphosphonium--.

Column 16, line 60, a period --.-- should be inserted after "added" and before "Once".

Column 18, in the Table, line 64, "1.0IE" should read --1.01E--.

UNITED STATES PATENT AND TRADEMARK OFFICE
CERTIFICATE OF CORRECTION

PATENT NO. : 5,431,845
DATED : July 11, 1995
INVENTOR(S) : Hashem Akhavan-Tafti

It is certified that error appears in the above—identified patent and that said Letters Patent is hereby corrected as shown below:

Column 20, line 6, "ant-goat" should read --anti-goat--.

Column 20, line 8, "ant-human" should read --anti-human--.

Column 21, line 8, the following should be inserted
--Fl-S = Tetradecanoylaminofluorescein
BDMQ = Poly(vinylbenzyl)benzyldimethylammonium chloride--.

Signed and Sealed this

Twentieth Day of February, 1996

Attest:

BRUCE LEHMAN

Attesting Officer

Commissioner of Patents and Trademarks